(12) United States Patent
Chadha

(10) Patent No.: US 8,551,196 B2
(45) Date of Patent: Oct. 8, 2013

(54) DISPENSING FORMULATION

(76) Inventor: Ajay Chadha, Tallahassee, FL (US)

( * ) Notice: Subject to any disclaimer, the term of this patent is extended or adjusted under 35 U.S.C. 154(b) by 99 days.

(21) Appl. No.: 13/084,190

(22) Filed: Apr. 11, 2011

(65) Prior Publication Data
US 2011/0212195 A1 Sep. 1, 2011

Related U.S. Application Data

(60) Continuation-in-part of application No. 11/809,654, filed on Jun. 1, 2007, now abandoned, which is a division of application No. 11/787,379, filed on Apr. 16, 2007, now abandoned.

(51) Int. Cl.
*C11C 5/00* (2006.01)
(52) U.S. Cl.
USPC ........................................................... 44/275

(58) Field of Classification Search
USPC ........................................................... 44/275
See application file for complete search history.

(56) References Cited

U.S. PATENT DOCUMENTS

| | | | | |
|---|---|---|---|---|
| 5,578,089 A * | 11/1996 | Elsamaloty | ...................... | 44/275 |
| 6,500,218 B1 * | 12/2002 | Fan | .................................. | 44/275 |
| 6,706,081 B2 * | 3/2004 | Mack et al. | ...................... | 44/275 |

* cited by examiner

*Primary Examiner* — Cephia D Toomer
(74) *Attorney, Agent, or Firm* — J. Wiley Horton; Adrienne C. Love

(57) ABSTRACT

A dispensing formulation for use in combination with an indirect heating source. In the preferred embodiment the dispensing formulation includes an additive such as a fragrance or a therapeutic compound, a hydrocarbon oil, having a flash point below 400° F. (generally between 330-400° F., most preferably between 330-355° F.) and a mixture of commercially available triblock polymers, such as Kraton® and Septon®.

19 Claims, 4 Drawing Sheets

DISPENSING FORMULATION

CROSS-REFERENCES TO RELATED APPLICATIONS

This is a continuation in part application of U.S. application Ser. No. 11/809,654, filed Jun. 1, 2007, now abandoned which in turn was a divisional application of U.S. patent application Ser. No. 11/787,379 filed Apr. 16, 2007, now abandoned. All applications name the same inventor.

STATEMENT REGARDING FEDERALLY SPONSORED RESEARCH OR DEVELOPMENT

Not Applicable.

MICROFICHE APPENDIX

Not Applicable.

BACKGROUND OF THE INVENTION

1. Field of the Invention

This invention relates to the field of candles. More specifically, the invention comprises a dispensing formulation for use in a candle assembly.

2. Description of the Related Art

Candles have been used for illumination and other purposes for many centuries. Oftentimes, candles are used to dispense fragrances or compounds which are therapeutic in nature. These fragrances or compounds are typically incorporated into a gel or wax-based fuel for use in a candle which contains a heat source, such as a wick. The fragrance or compound is released as the candle formulation is volatized.

There are various disadvantages to the prior art candle gel or wax-based formulations. Many fragrance oils or therapeutic compounds are volatile liquids and tend to have a low flash point. The flash point is the lowest temperature at which there will be enough flammable vapor to ignite when an ignition source is applied. For example, Eucalyptol (a major component of Eucalyptus Oil) has a flash point of 120° F. Similarly, Rosemary has a flash point of 106° F. At these "flash points" the compound or fragrance will ignite when an ignition source, such as a lighted wick, is applied. Prior art gel formulations have been developed for use as a fuel in a candle, wherein the wick is in the body of the formulation and the formulation is in direct contact with the flame. Thus, prior art gel compositions teach the use of high flash point hydrocarbon oil (i.e. hydrocarbon oil having a carbon chain of 18 to 30 carbons) in combination with the low flash point fragrance oils or therapeutic compounds to minimize the risk of candle fire (U.S. Pat. No. 5,964,905 to Camp et al.; U.S. Pat. No. 6,582,484 to Wilson). Higher flash point oils tend to have high viscosity and can be expensive in cost. Candle gels made with high viscosity oils are also slow to pump from mix tanks to the site where the candles will be poured. It follows that these oils require more power to pump than lower viscosity oils, which move quickly and efficiently through pumps. Thus, the manufacturing process of higher flash point oils (high viscosity) is more expensive overall and less efficient than those gels having lower flash point oils (low viscosity).

To reduce the overall cost of candle, among other advantages, it would be desirable to mix the fragrance oils with lower flash point hydrocarbon oil gels which tend to have lower viscosity and are easy to transport in a manufacturing process. These lower viscosity oils are lower in cost. When exposed to an indirect heat source, such oil gels will melt fast to dissipate the aroma and spread the fragrance in the room faster. Such a dispensing formulation has the ability to retain the fragrance for repeated use. These indirectly heated dispensing formulations will also have a melt pool temperature that would be considerably lower than the flash point of the mixture of fragrance oil and hydrocarbon oil, thereby eliminating the fire hazard. Such a candle would not be used as a fuel (i.e. exposed directly to the flame), but instead act solely as a dispensing formulation. It is also important that the gel formulations are not too "soft" that the gel suffers from creep and risks pouring out of the container during transport.

Thus, it would be desirable to provide an active chemical dispensing formulation which transports well and readily releases low flashpoint fragrances and therapeutic compounds at high concentrations when indirectly heated, without the risk of fire.

BRIEF SUMMARY OF THE INVENTION

The present invention comprises a dispensing formulation for use in combination with an indirect heating source. In the preferred embodiment the dispensing formulation includes an additive such as a fragrance or a therapeutic compound, a hydrocarbon oil, having a flash point below 400° F. (generally between 330-400° F., most preferably between 330-355° F.) and a mixture of commercially available triblock polymers, such as Kraton® and Septon®.

Dispensing formulation can be used in a candle container assembly 10. The assembly includes an outer container, a medial container situated within and attached to the outer container, and a dispensing formulation between the outer container and the medial container. The assembly further includes an inner container which contains a heat source such as a candle. The inner container may be removed and replaced when the candle is completely consumed. Additionally, dispensing formulation can be used in a candle container designed to be used in conjunction with an electric candle warmer as opposed to a wick-based candle.

REFERENCE NUMERALS IN THE DRAWINGS

| 10 | candle container assembly | 12 | outer container |
|----|---------------------------|----|-----------------|
| 14 | medial container          | 16 | inner container |
| 18 | base                      | 20 | base            |
| 22 | fuel composition          | 24 | wick            |
| 26 | dispensing formulation    |    |                 |

DETAILED DESCRIPTION OF THE INVENTION

Figure 1:
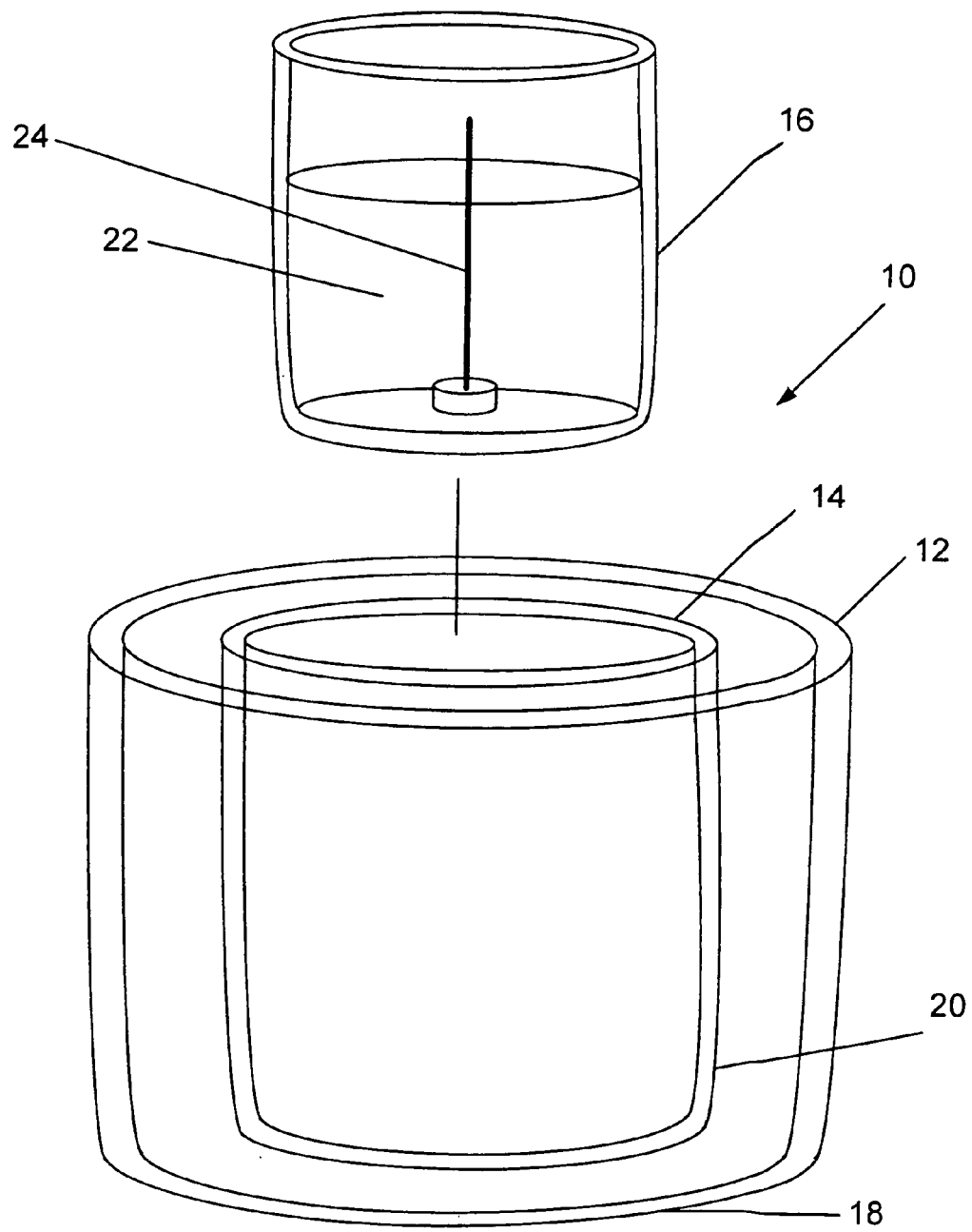
FIG. 1 is an exploded view, showing the candle container assembly.

The dispensing formulation of the present invention is composed to be useful in an application including an indirect heating source, such as a candle container assembly 10 illustrated in FIG. 1 or a candle warmer (such as, for example, the candle warmer disclosed by U.S. Patent Application Publication No. US 2007/0047931 to Niemeyer). For purposes of the present invention "indirect heating source" will mean a heat source which must act on another object or material before acting on the present dispensing formulation. Thus, if the heat source must act on the glass containing the dispensing formulation prior to acting on the dispensing formulation, it should be considered an "indirect heating source" for purposes of the present invention.

Figure 2:
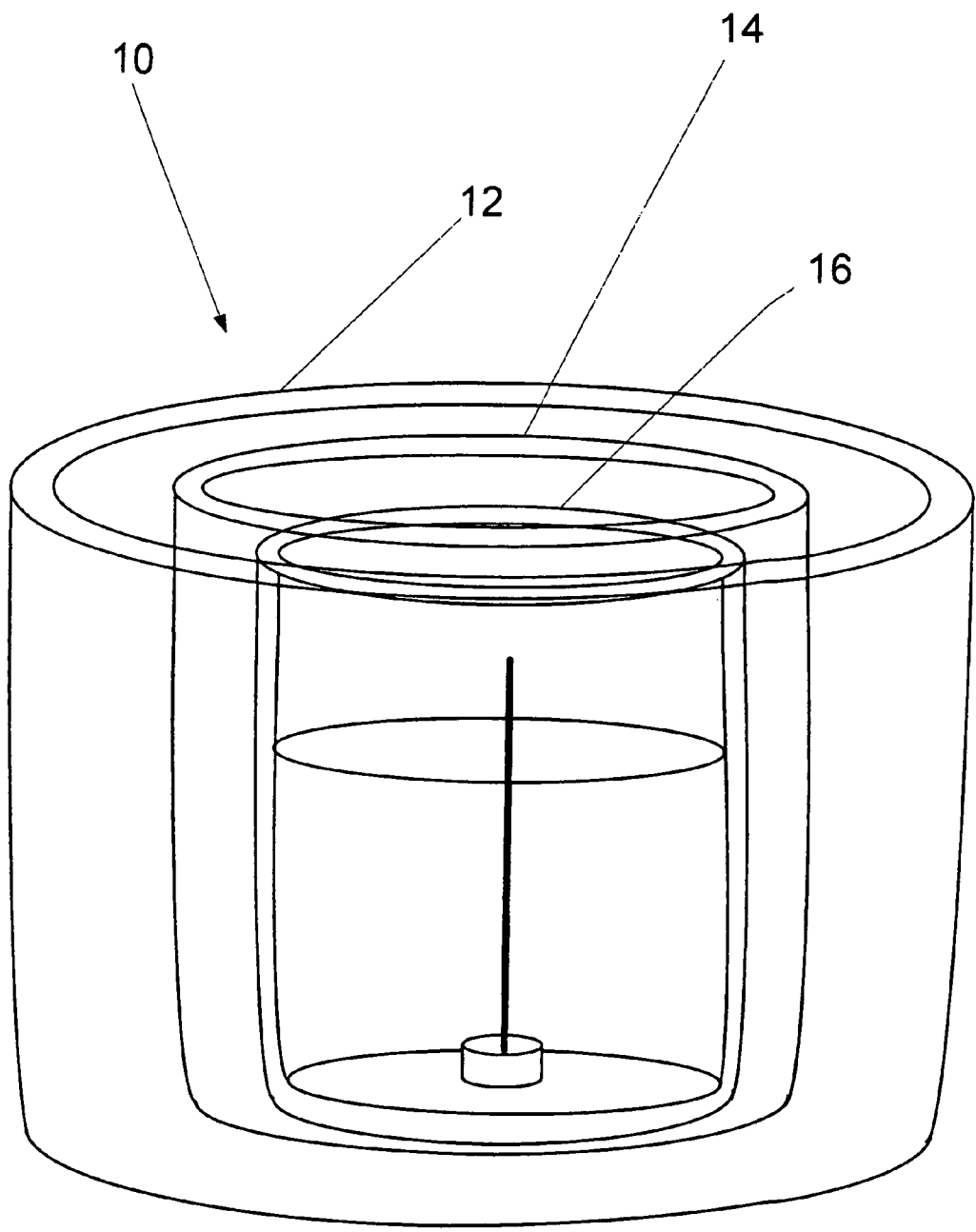
FIG. 2 is a perspective view, showing the present invention in an assembled state.

Candle container assembly 10 is one example of a use in which the present dispensing formulation 26 is used in a manner wherein dispensing formulation 26 is exposed to an indirect heating source. Candle container assembly 10 includes outer container 12, medial container 14 situated within and attached to outer container 12, and removable inner container 16. Base 20 of medial container 14 and base 18 of outer container 12 may be attached together with an adhesive or the components may be thermally fused together or simply held in place with the assistance of a gel or wax. Inner container 16 includes fuel composition 22 and wick 24. Many different fuel compositions for candles are known in the art. For example inner container 16 could contain a standard wax candle. Inner container 16 may be removed and replaced when the candle is completely consumed. The present dispensing formulation 26 should not be used as a fuel composition within inner container 16, as will be described herein FIG. 2 shows inner container 16 situated within medial container 14. The reader will appreciate that the candle is contained within three distinct containers when candle container assembly 10 is assembled.

Figure 3:
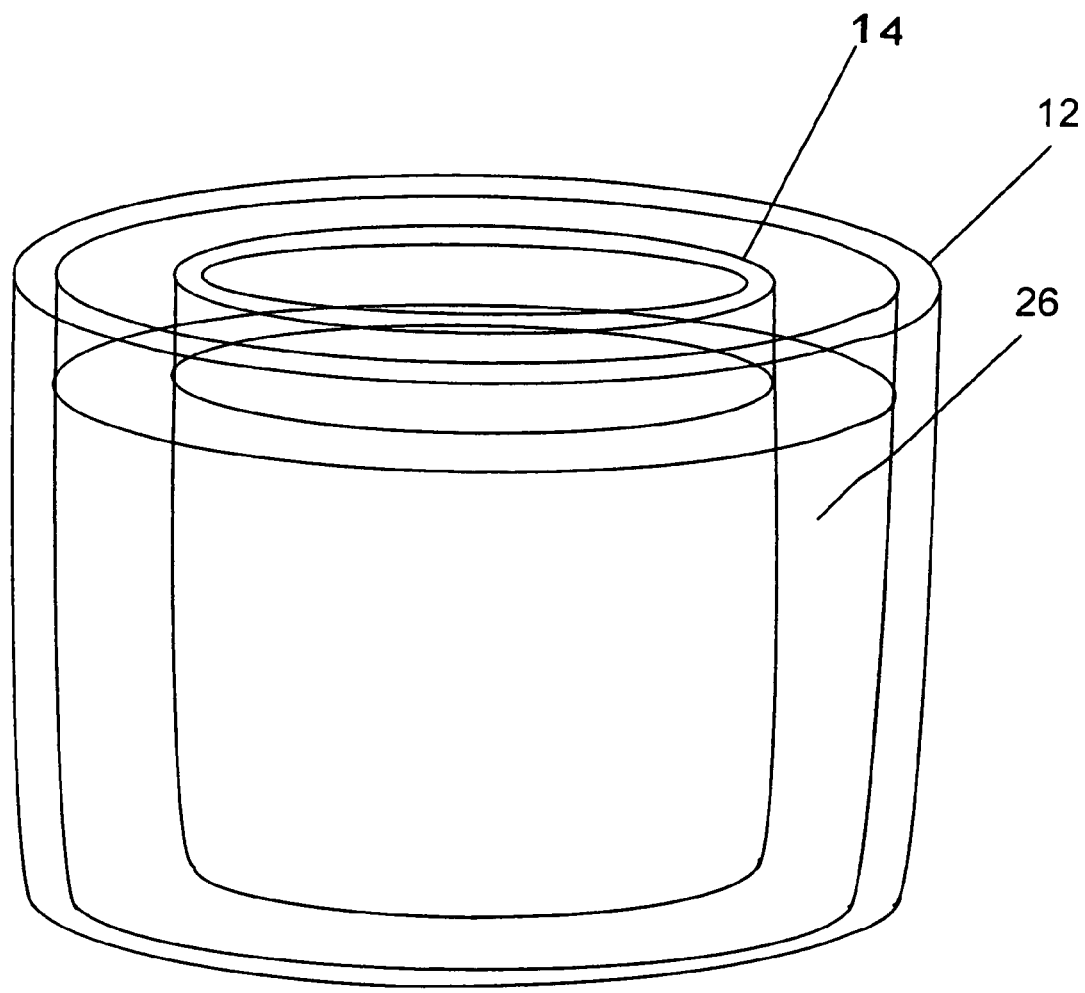
FIG. 3 is a perspective view, showing the present invention with the inner container removed.
Figure 4:
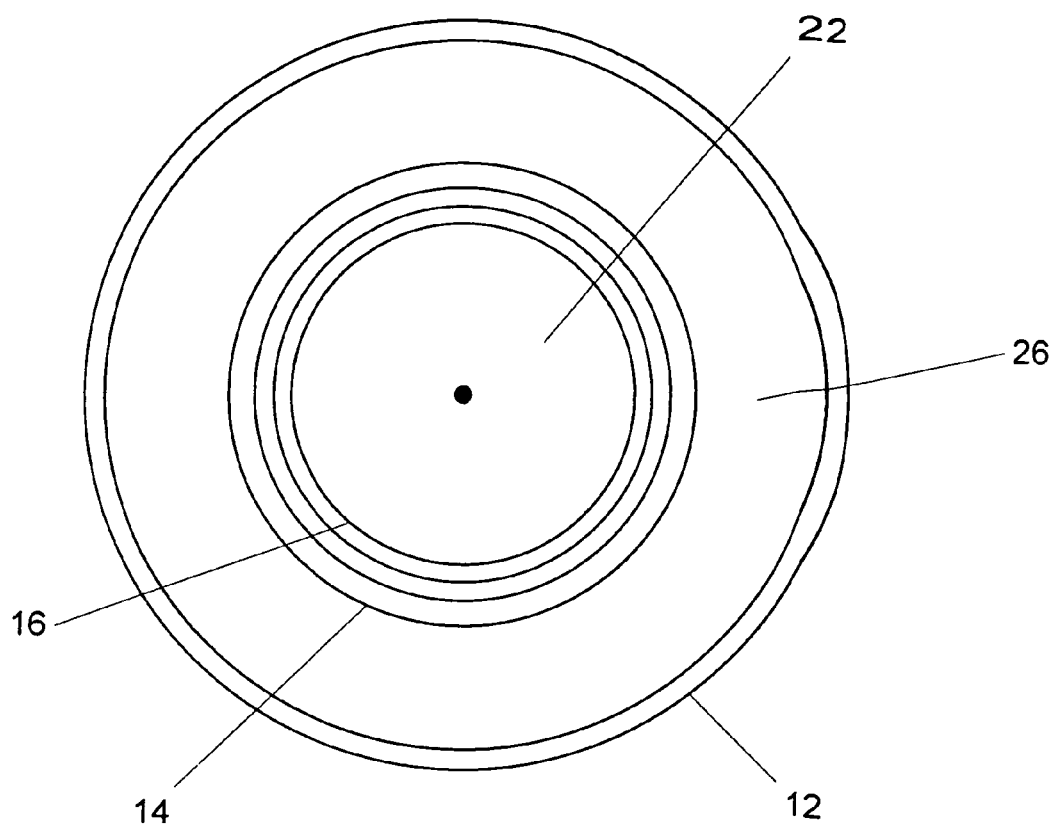
FIG. 4 is a top view, showing the present invention.

Turning now to FIG. 3 (which omits the inner container and candle), the reader will note that dispensing formulation 26 has been added between outer container 12 and medial container 14. FIG. 4 is a top view showing the candle container assembly. Dispensing formulation 26 is contained between outer container 12 and medial container 14. Candle 22 is contained within inner container 16. Thus, in order to heat gel 26, heat generated from burning candle 22 must pass through inner container 16, medial container 14 and the space between the two components. Thus, dispensing formulation 26 is exposed to an "indirect heating source."

Dispensing formulation 26 is preferably comprised of a hydrocarbon oil, having a flash point below 400° F., commercially available tri-block polymers and additives such as a chemical additive which is to be volatilized. Many different chemical additives can be used in such a dispensing formulation including well-known fragrances, insect repellents, or therapeutic oils (such as eucalyptus oil). Dispensing formulation 26 is useful in a candle application which is exposed to an indirect heating source, such as candle container assembly 10 illustrated herein. The present dispensing formulation is not formulated to act as a fuel and thus, should not be exposed to a direct heat source, such as a wick.

The heat generated by burning the candle in inner container 16 vaporizes some of the chemical additive and dispensing formulation 26 releases these vapors to the environment over time. Candle container assembly 10 may be exposed to more candle-burning hours in comparison to prior art candle containers (because of the replaceability of inner container 16). The new dispensing formulation 26 is capable of releasing additive vapors consistently over the length of time it takes to burn multiple candles is needed. Several embodiments of such a dispensing formulation will now be considered in greater detail.

The objectives of the present invention may be accomplished using a dispensing formulation comprising di-block, tri-block, multi-block or radial copolymers or their mixtures. The styrenic di-block and tri-block copolymers are most compatible with hydrocarbon oils in varying proportions. Most preferred are the styrenic tri-block copolymers. Varying the concentration of styrenic tri-block copolymers can control the strength and the transport properties of the dispensing formulations.

In the preferred embodiment, the dispensing formulation comprises a tri-block polymer or a mixture of two tri-block polymers in hydrocarbon oil (mineral oil/white oil). The tri-block polymers, commercially known as Kraton® G-1650 and Septon® 4033 are most preferred polymers for the present invention. It is important that the hydrocarbon oil (mineral oil/white oil) used in the present invention has a flash point below 400° F. (generally between 330-400° F., but most preferably between 330-355° F.) but is not volatile between room temperature and 140° F., and more preferably the hydrocarbon oil is not volatile below 200° F. The lower flash point oils with lower viscosity result in dispensing formulations having the ability to release strong fragrance when exposed to an "indirect heating source." Further, the present dispensing formulation will have a melt pool temperature that would be considerably lower than the flash point of the dispensing formulation mixture itself, thereby eliminating any fire hazard. By adding the tri-block polymers, further described below, the present dispensing formulation can still remain stiff and transportable at room temperature. Kraton® G-1650, sold by Kraton Polymers LLC of Houston, Tex., is a polymer having a Styrene-Ethylene-Butylene-Styrene (SEBS) structure. The G group of Kraton® rubbers are compatible with paraffinic and naphthionic oils. These tri-block copolymers are reported as taking up more than 20 times their weight in oil and make a product which can vary in consistency from a "Jello" to a strong elastic rubbery material.

Septon® 4033 is a thermoplastic rubber sold by Kuraray Co., Ltd. of Japan. The polymer has a Styrene-Isoprene-Butadiene-Styrene structure. The Septon® 4033 rubber molecule is hydrogenated styrene block polymer with 2-methyl-1,3-butadiene and 1,3-butadiene. Septon® 4033 has polystyrene end blocks and an elastomeric midblock.

For the purposes of the following examples, the reader should note that dispensing formulation 26 generally includes a gel and an additive. In the preferred embodiment, the gel includes 6.4% weight Kraton® G-1650, 1.6% weight Septon® 4033, 0.01-0.05% weight butylated hydroxytoluene, with the balance comprising a hydrocarbon oil (such as mineral oil) having a flash point between 330-355° F. The butylated hydroxytoluene acts as an antioxidant and prevents "yellowing" of the hydrocarbon oil which degrades the oils appearance, smell, and chemical properties. The gel composition can include up to 1% weight butylated hydroxytoluene.

It is preferred that the gel contain Kraton® G-1650 in a total gel weight range of 30.0%-0.5%. It is also preferred that the gel contain Septon® 4033 in a total gel weight range of 14.5%-0.5%. The combined weight percentage of Kraton® G-1650 and Septon® 4033 is preferably in the range of 30.0%-0.5%, with a more preferred range of 15%-6%, and the most preferred gel being approximately 8% weight Kraton® G-1650 and Septon® 4033.

The mixture of Kraton® G-1650 and Septon® 4033 may be adjusted to achieve a product with the desired properties. These polymers are added for superior cross linking and to reduce creep. Creep is a property of a gel which allows the gel to flow and potentially pour out of the container during transportation.

Once the gel is prepared, an additive is preferably added to the gel. In the presence of an indirect heating source the additive is vaporized out of the gel dispensing formulation.

As mentioned previously, the additive can include fragrances, insect repellents, therapeutic oils, coloring agents and/or UV stabilizers. If the additive is a chemical substrate such as a fragrance, insect repellent or therapeutic oil, it is preferred that the additive comprise 60%-0.05% of the total additive gel 26, with a more preferred range of 15% to 0.05%.

The example below illustrates the invention and shows the use of low flash point hydrocarbon oil in making a fast melting dispensing formulation that is capable of dispensing low flash point fragrance oils. This example is for illustration only. It should not be considered to limit the scope of the invention.

Example 1

Two refillable candles (as shown in FIG. 1) were prepared using white mineral oils from Sonneborn LLC of Mahwah, N.J. with different flash points. The two oils used were Britol® 7NF (for Candle 1) and Semtol® 350 (for Candle 2). The properties of the two oils are provided in Table 1 below.

TABLE 1

White Mineral Oil Properties

| PROPERTIES | TEST METHOD | Britol 7NF | Semtol 350 |
|---|---|---|---|
| Specific Gravity @ 25° C./25° C. | ASTM D4052 | 0.835/0.862 | 0.869/0.885 |
| Kin. Viscosity @ 40° C., mm2/s | ASTM D445 | 10.8/13.6 | 64.0/70.0 |
| Flash Point deg ° F. | D-92 | 347° F. | 428° F. |

Preparation technique, polymer concentration and fragrance load were kept same for both the candles. The discussion below will provide the details of the manufacturing technique.

Preparation of Dispensing Formulation:

The white mineral oil was added to a container with constant stirring. The two polymers, Septon® 4033 (1.6 wt %) and Kraton® G1650 (6.4 wt %) were added slowly to the oil and temperature was raised to 250° F. to dissolve the polymers in the oil. The solution was cooled to 200° F. and Eucalyptus oil (Flash Point 127° F.) was added at 6 wt % load with constant stirring. At this point, the mixture was poured between the outer container 12 and medial container 14 (FIG. 1) and allowed to cool and solidify. The gel of Candle 1 was considerably softer as compared to gel of Candle 2.

A tealight was prepared using a standard polycarbonate cup filled with IGI 4630 wax. A standard 1" wick (#4420C) from Atkins & Pearce with 20 mm tab and 3.8 mm neck height was used for the tests.

The two refillable candles were tested separately for fragrance dissipation in a closed room with dimensions 5 ft wide, 8 ft high and 8 ft length. Fragrance intensity and melting of gel were observed in time intervals of 15 minutes for 1 hour. A 4" long needle was used to poke the gel from the top to check the gel hardness. The fragrance emanating from the gel was observed by human test subjects by simply smelling the candle at an approximate distance of 6" from the candle. A fragrance strength number on a scale of 1 to 10 was given to describe the strength of fragrance emanating from the gel. The results of the test are shown in Table 2.

TABLE 2

Gel Melting and Fragrance Strength at Different Time Intervals.

| | Oil Used | Gel Form (Before Lighting) | Time (min) | | | | |
|---|---|---|---|---|---|---|---|
| | | | 0 min | 15 min | 30 min | 45 min | 60 min |
| Candle 1 | Britol 7NF, Flash Point 347° F. | Soft Gel | The candle smells strong Strength # 9. | Gel starts to melt. Small pool of melted gel observed near the medial container #14. Strength # 9. | Gel melted completly between medial container 14 & outer container 12. Strength #10. | Completely melted Gel. Strength # 10. | Completely Melted Gel. Strength # 10. |
| Candle 2 | Semtol 350, Flash Point 428° F. | Hard Gel | Slight smell observed from candle. Strength # 3. | No gel melting observed. The candle did not smell strong. Strength #3. | Slight gel softening observed near medial container # 14. Strength #3. | Small pools of melted gel observed near the medial container #14. Strength # 4. | The gel started to melt uniformly near the medial container # 14. Gel remains hard near the outer container 12. Strength # 4. |

Candle 1, having a low flash point hydrocarbon oil (347° F.), melts fast and releases strong fragrance when exposed to an indirect heating source. However, candle 2, having a high flash point hydrocarbon oil (428° F.), melts slow and does not release a strong fragrance when exposed to an indirect heating source.

The preceding description contains significant detail regarding the novel aspects of the present invention. It is should not be construed, however, as limiting the scope of the invention but rather as providing illustrations of the preferred embodiments of the invention. Thus, the scope of the invention should be fixed by the following claims, rather than by the examples given.

The invention claimed is:

1. A dispensing formulation for a candle container assembly comprising:
   a. a gel, including i. a mixture of a polymer having a Styrene-Isoprene-Butadiene-Styrene structure and a polymer having a Styrene-Ethylene-Butylene-Styrene structure, said mixture having a weight percentage in the range of 0.5 to 30 percent of said gel;
   ii. a hydrocarbon oil having a flash point below 400° F.;
  b. an additive mixed with said gel, said additive selected from a group consisting of:
   i. a fragrance;
   ii. an insect repellent; and
   iii. a therapeutic oil;
  c. wherein said dispensing formulation vaporizes said additive when exposed to an indirect heat source.

2. The dispensing formulation of claim 1, wherein said hydrocarbon oil has a flash point between 330-355° F.

3. The dispensing formulation of claim 1, said mixture of a polymer having a Styrene-Isoprene-Butadiene-Styrene structure and a polymer having a Styrene-Ethylene-Butylene-Styrene structure having a weight percentage in the range of 6 to 15 percent of said gel.

4. The dispensing formulation of claim 3, said mixture of a polymer having a Styrene-Isoprene-Butadiene-Styrene structure and a polymer having a Styrene-Ethylene-Butylene-Styrene structure having a weight percentage of approximately 8 percent of said gel.

5. The dispensing formulation of claim 4, said gel comprising approximately 6.4% weight a polymer having a Styrene-Ethylene-Butylene-Styrene structure and approximately 1.6% weight a polymer having a Styrene-Isoprene-Butadiene-Styrene structure.

6. The dispensing formulation of claim 1, wherein said polymer having a Styrene-Ethylene-Butylene-Styrene structure comprises 0.5 to 14.5 percentage of the weight of said gel.

7. The dispensing formulation of claim 1, wherein said polymer having a Styrene-Isoprene-Butadiene-Styrene structure comprises 0.5 to 14.5 percentage of the weight of said gel.

8. The dispensing formulation of claim 1, said additive comprising 0.05% to 15% of the weight of said dispensing formulation.

9. The dispensing formulation of claim 1, further comprising butylated hydroxytoluene, said butylated hydroxytoluene comprising 0.01 to 1% weight of said gel.

10. The dispensing formulation of claim 8, said butylated hydroxytoluene comprising 0.01 to 0.05% weight of said gel.

11. A dispensing formulation for a candle container assembly comprising:
  a. a gel, including
   i. a polymer, selected from a group consisting of a diblock polymer, a triblock polymer, a radial block copolymer and a multiblock copolymer;
   ii. a hydrocarbon oil, said hydrocarbon oil having a flash point below 400° F.;
  b. an additive mixed with said gel, said additive selected from a group consisting of
   i. a fragrance;
   ii. an insect repellent; and
   iii. a therapeutic oil;
  c. wherein said dispensing formulation vaporizes said additive when exposed to an indirect heat source.

12. The dispensing formulation of claim 11, said gel including a mixture of a polymer having a Styrene-Isoprene-Butadiene-Styrene structure and a polymer having a Styrene-Ethylene-Butylene-Styrene structure triblock copolymers having a weight percentage in the range of 6 to 15 percent of said gel.

13. The dispensing formulation of claim 11, wherein said polymer having a Styrene-Ethylene-Butylene-Styrene structure comprises 0.5 to 14.5 percentage of the weight of said gel.

14. The dispensing formulation of claim 11, said additive comprising 0.05% to 15% of the total weight of said dispensing formulation.

15. The dispensing formulation of claim 11, said polymer being a styrenic triblock polymer.

16. A dispensing formulation for a candle container assembly comprising:
  a. a gel, including
   i. a polymer having a Styrene-Ethylene-Butylene-Styrene structure, said polymer having a weight percentage in the range of 0.5 to 30 percent of said gel; and
   ii. a hydrocarbon oil, wherein said hydrocarbon oil has a flash point below 400° F.;
  b. an additive mixed with said gel, said additive selected from a group consisting of:
   i. a fragrance;
   ii. an insect repellent; and
   iii. a therapeutic oil;
  c. wherein said dispensing formulation vaporizes said additive when exposed to an indirect heat source.

17. The dispensing formulation of claim 16, wherein said hydrocarbon oil has a flash point between 330-355° F.

18. The dispensing formulation of claim 16, wherein said polymer having a Styrene-Ethylene-Butylene-Styrene structure has a weight percentage in the range of 6 to 15 percent of said gel.

19. The dispensing formulation of claim 18, wherein said polymer having a Styrene-Ethylene-Butylene-Styrene structure has a weight percentage of approximately 8 percent of said gel.

* * * * *